United States Patent
Hof

(10) Patent No.: US 6,586,634 B1
(45) Date of Patent: Jul. 1, 2003

(54) PROCESS FOR THE PREPARATION ON (1S, 2R)-1-AMINO-2-INDANOL-(R,R)-TARTRATE METHANOL SOLVATE

(75) Inventor: Robert Patrick Hof, Venlo (NL)

(73) Assignee: DSM N.V., Heerlen (NL)

( * ) Notice: Subject to any disclaimer, the term of this patent is extended or adjusted under 35 U.S.C. 154(b) by 62 days.

(21) Appl. No.: 09/095,932

(22) Filed: Jun. 12, 1998

(30) Foreign Application Priority Data

Jun. 13, 1997 (NL) ............................................. 1006305

(51) Int. Cl.[7] ..................... C07C 211/00; C07C 209/00; C07C 213/10

(52) U.S. Cl. ........................ 564/425; 564/424; 564/305; 564/315

(58) Field of Search ................................ 564/304, 315, 564/424, 425

(56) References Cited

U.S. PATENT DOCUMENTS

| | | | | |
|---|---|---|---|---|
| 5,420,353 A | | 5/1995 | Verhoeven ................... | 564/399 |
| 5,449,830 A | * | 9/1995 | Verhoeven et al. .......... | 564/400 |
| 5,489,710 A | * | 2/1996 | Verhoeven et al. .......... | 564/402 |
| 5,605,819 A | * | 2/1997 | Chartrain et al. ............ | 435/123 |
| 5,612,484 A | * | 3/1997 | Askin et al. ................. | 544/360 |
| 5,618,937 A | * | 4/1997 | Askin et al. ................. | 544/360 |

FOREIGN PATENT DOCUMENTS

EP    0 541 164 A1    12/1993

OTHER PUBLICATIONS

Thompson, et al. Synthesis and Antiviral Activity of a Series of HIV–1 Protease Inhibitors with Functionality Tethered to the P1 or P1' Phenyl Substituents: X–ray Crystal Structure Assisted Design, J. Med. Chem. 1992, 35, 1685–1701.

* cited by examiner

Primary Examiner—Alan L. Rotman
Assistant Examiner—T. V. Oh
(74) Attorney, Agent, or Firm—Pillsbury Winthrop LLP

(57) ABSTRACT

Process for the preparation of (1S,2R)-1-amino-2-indanol-(R,R)-tartrate methanol solvate, in which in a solvent a mixture of enantiomers of cis-1-amino-2-indanol reacts at an elevated temperature with (R,R)-tartaric acid and methanol and in which optically enriched (1S,2R)-1-amino-2-indanol-(R,R)-tartrate methanol solvate crystallizes out, after which the crystals are recovered, the recovery taking place at a temperature between 10 and 50° C. in the presence of 0–20 wt. % water relative to the amount of methanol plus solvent, on the understanding that if the reaction mixture is essentially free from water the recovery substantially takes place at a temperature between 30 and 50° C. Preferably the reactants are at least in part contacted with each other at an elevated temperature and only methanol is used as solvent. Preferably the amount of (1S,2R)-1-amino-2-indanol applied is between 0.02 and 0.1 g per ml of solvent.

The invention also relates to (1S,2R)-1-amino-2-indanol-(R,R)-tartrate methanol solvate crystals having a particle size larger than 95 μm, expressed as D[v, 0.9], in particular those in which the enantiomeric excess of (1S,2R)-1-amino-2-indanol-(R,R)-tartrate relative to (1S,2R)-1-amino-2-indanol-(R,R)-tartrate is higher than 96%, as well as to application of (1S,2R)-1-amino-2-indanol-(R,R)-tartrate methanol solvate in the preparation of AIDS inhibitors, in particular indinavir sulphate.

9 Claims, No Drawings

PROCESS FOR THE PREPARATION ON (1S, 2R)-1-AMINO-2-INDANOL-(R,R)-TARTRATE METHANOL SOLVATE

FIELD OF THE INVENTION

The invention relates to a process for the reparation of (1S,2R)-1-amino-2-indanol-(R,R)-tartrate methanol solvate, in which in a solvent a mixture of enantiomers of cis-1-amino-2-indanol reacts at an elevated temperature with (R,R)-tartaric acid and methanol and in which optically enriched (1S,2R)-1-amino-2-indanol-(R,R)-tartrate methanol solvate crystallizes out, after which the crystals are recovered.

BACKGROUND INFORMATION

Such a process is known from U.S. Pat. No. 5,420,353, in which in a highly diluted solution and in a water-free environment (<0.1 $H_2O$), (1S,2R)-1-amino-2-indanol-(R,R)-tartrate methanol solvate crystals are obtained after cooling to 20° C.

It is a drawback of the known process, however, that it has to be carried out with a high degree of dilution.

SUMMARY AND OBJECTS OF THE INVENTION

The invention aims to provide a process whereby at a much higher concentration than in the known process (1S, 2R)-1-amino-2-indanol-(R,R)-tartrate methanol solvate can be obtained in solid form.

This is achieved according to the invention in that the recovery takes place at a temperature between 10 and 50° C. in the presence of 0–20 wt. % water relative to the amount of methanol plus solvent, on the understanding that if the reaction mixture is essentially free from water the recovery substantially takes place at a temperature between 30 and 50° C.

The fact is that the applicant has found that if in the known process a high concentration of cis-1-amino-2-indanol is used it often happens that the undesired enantiomer of cis-1-amino-2-indanol, (1R,2S)-1-amino-2indanol, crystallizes out as diastereomeric tartrate, which is highly undesirable because of the unpredictability of this happening. In addition, the applicant surprisingly has found that when the recovery took place at an elevated temperature this undesired effect did not occur any more, and that this undesired effect did not occur either when the recovery was yet carried out at the same low temperature, but in the presence of a certain amount of water. Further it was found that the process according to the invention enabled a higher yield to be obtained and that the crystals could be obtained with a higher enantiomeric excess (e.e.) of (1S,2R)-1-amino-2-indanol, present in the salt, relative to the (1R,2S) enantiomer, compared with the results of the known process.

DETAILED DESCRIPTION OF THE INVENTION

A process for the preparation of (1S,2R)-1-amino-2-indanol-(R,R)-tartrate methanol solvate, in which in a solvent a mixture of enantiomers of cis-1-amino-2-indanol reacts at an elevated temperature with (R,R)-tartaric acid and methanol and in which optically enriched (1S,2R)-1-amino-2-indanol-(R,R)-tartrate methanol solvate crystallizes out, after which the crystals are recovered, wherein the recovery takes place at a temperature between 10 and 50° C. in the presence of 0–20wt. % water relative to the amount of methanol plus solvent, on the understanding that if the reaction mixture is essentially free from water the recovery substantially takes place at a temperature between 30 and 50° C.

Preferably solutions of the reactants are first at least partially heated, then contacted with each other at an elevated temperature and next, after the reaction, the reaction mixture is cooled down. This offers the important advantage that with this process according to the invention significantly larger (1S,2R)-1-amino-2-indanol-(R,R)-tartrate methanol solvate crystals can be obtained than with the known process, which makes it easier to recover the crystals. The invention also relates to (1S,2R)-1-amino-2-indanol-(R,R)-tartrate methanol solvate crystals having such a particle size and particle size distribution that the D[v,0, 9]—defined as the diameter in comparison with which 90% of the particles are smaller and 10% are larger—is larger than 95 µm, in particular larger than 110 µm, more in particular larger than 120 µm. The particle size is determined using a Malvern 2600 apparatus; the quantities applied are explained in further detail in the manual going with the apparatus.

The process according to the invention is preferably carried out at relatively high concentrations; in particular, the applied amount of (1S,2R)-1-amino-2-indanol is 0.02 to 0.1 gram per ml of solvent, preferably between 0.05 and 0.08 g/ml.

The reaction is carried out in the presence of methanol. Preferably therefore methanol is used at the only organic solvent. Optionally, however, other organic solvents can be used as co-solvents besides methanol.

A suitable co-solvent is in principle any solvent which is inert in the reaction mixture, in which cis-1-amino-2-indanol and tartaric acid dissolve to an important extent and in which the salt of (R,R)-tartaric acid and (1S,2R)-1-amino-2-indanol as methanol solvate is poorly soluble, for instance i-butanol, n-butanol, dimethylformamide (DMF) or acetonitrile.

In addition the reaction mixture can contain water as well. The amount of water in the reaction mixture is between 0 and 20 wt. % relative to the amount of methanol plus organic solvent present in the reaction mixture. If the reaction mixture is essentially free from water, for instance contains less than 5 wt. % of water relative to methanol, then recovery takes place at a temperature between 30 and 50° C., in particular between 30 and 37° C. Preferably the reaction mixture contains 2–15 wt. % of water relative to the amount of methanol. The larger the amount of water in the reaction mixture, the lower the temperature at which the recovery can take place. The recovery will in practice mostly take place at a temperature between 10 and 40° C.

The reaction of the mixture of enantiomers of cis-1-amino-2-indanol takes place at an elevated temperature, preferably at a temperature between 30 and 150° C., in particular between 55 and 80° C.

The starting material used in the process according to the invention is a mixture of-enantiomers of cis-1-amino-2-indanol, in particular a racemic mixture of cis-1-amino-2-indanol. In the framework of the invention a racemic mixture is understood to be a mixture in which the two enantiomers are present in equal amounts or in which one of the enantiomers is present with a minor excess, for instance an e.e. of less than 10%, over the other enantiomer.

The tartaric acid is preferably applied in a molar excess of (R,R)-tartaric acid relative to the mixture of enantiomers of cis-1-amino-2-indanol present in the reaction mixture, for instance 1.05–2.05 equivalents. In addition, due to addition of a strong acid, for instance hydrochloric acid, the optimum amount of (R,R)-tartaric acid to be applied can be lowered to 1 equivalent relative to the amount of (1S,2R)-1-amino-2-indanol. The total amount of acid to be added is at least 1 equivalent, relative to the mixture of enantiomers of cis-1-amino-2-indanol. The enantiomeric excess of (R,R)-tartaric acid to be applied is preferably as large as possible, for instance greater than 95%, in particular greater than 99%.

In a preferred embodiment of the process, in which racemic cis-1-amino-2-indanol is split up, a certain portion, for instance 15–50%, of the total amount of racemic cis-1-amino-2-indanol (wet) and (R,R)-tartaric acid is started from; after addition of methanol the mixture is heated up, for instance to reflux temperature. In order to ensure thorough mixing of the reaction components, the reactor contents are stirred. Then the rest of the cis-1-amino-2-indanol is supplied in the form of a solution in methanol, followed by cooling of the mixture and recovery of the crystals.

The (1S,2R)-1-amino-2-indanol-(R,R)-tartrate methanol solvate thus obtained can subsequently be subjected to a desalting step, resulting in optically active (1S,2R)-1-amino-2-indanol. (1S,2R)-1-amino-2-indanol is an important intermediate in the preparation of pharmaceuticals, for instance AIDS inhibitors, in particular indinavir sulphate, such as for instance described in U.S. Pat. No. 5,420,353, or by Thompson et al. in J. Med. Chem., Vol. 35 (1992), 1685.

The invention will be further elucidated by means of the examples, without being restricted thereto.

COMPARATIVE EXPERIMENT LOW CONCENTRATION

Racemic cis-1-amino-2-indanol (25.1 g) was dissolved in 375 ml of ethanol. At room temperature a solution of (R,R)-tartaric acid (27.5 g) in 375 ml of methanol was added. The water content was less than 0.1 wt. % relative to methanol. Then the mixture was heated to 60° C. and then cooled down again to 20° C. The solid was recovered by filtration and washed with 100 ml of methanol. After drying, 23.7 g of (1S,2R)-1-amino-2-indanol-(R,R)-tartrate methanol solvate were obtained with an e.e. of 93.1%. D[v, 0.9]=92.7 µm (measured with a Malvern 2600 apparatus).

Example I

Racemic cis-1-amino-2-indanol (22.5 g, water wet, content 83.2%) was suspended with (R,R)-tartaric acid (65 g) in 120 ml of methanol of 60° C. After stirring for 1.5 hours at 60° C., 210 ml of methanol were added and the mixture was brought to reflux. At reflux a solution of racemic cis-1-amino-2-indanol (42.4 g, water wet, content 83.2%) in 120 ml of hot methanol was added. Stirring of the mixture was continued for half an hour at reflux and then it was cooled down again to 33° C. Methanol (10 ml) was added and after continued stirring (overnight) the solid was isolated by filtration and washed twice with 120 ml of methanol. After drying, 54.3 g of (1S,2R)-1-amino-2-indanol-(R,R)-tartrate methanol solvate were obtained with an e.e. of 97.5%. D[v, 0.9]=147.1 µm (measured with a Malvern 2600 apparatus).

Example II

Racemic cis-1-amino-2-indanol (66.6 g, water wet, content 81.1%) and 65 g of (R,R)-tartaric acid in 360 ml of methanol with 20 ml of water were brought to reflux. Stirring of the mixture was continued for one hour at reflux and then it was cooled down again to 20° C. The solid was isolated by filtration and washed twice with 120 ml of methanol. After drying, 54.3 g of (1S,2R)-1-amino-2-indanol-(R,R)-tartrate methanol solvate were obtained with an e.e. of 96.7%.

Example III

Racemic cis-1-amino-2-indanol (66.6 g, water wet, content 81.1%) was dissolved in 180 ml of methanol with 10 ml of DMF at reflux. Then 65 g of (R,R)-tartaric acid dissolved in 200 ml of methanol were added. Stirring of the mixture was continued for one hour at reflux and then it was cooled down again to 20° C. and isolation by filtration was effected. The solid was washed twice with 120 ml of methanol. After drying, 54.8 g of (1S,2R)-1-amino-2-indanol-(R,R)-tartrate methanol solvate were obtained with an e.e. of 97.0%.

Example IV

Racemic cis-1-amino-2-indanol (66.6 g, water wet, content 81.1%) was dissolved in 390 ml of methanol with 10 ml of water. 65 g of (R,R)-tartaric acid were added in portions at 60° C. Stirring of the mixture was continued for one hour at reflux and then it was cooled down again to 20° C. The solid was isolated by filtration and washed twice with 120 ml of methanol. After drying, 56.2 g of (1S,2R)-1-amino-2-indanol-(R,R)-tartrate methanol solvate were obtained with an e.e. of 97.2%.

What is claimed is:

1. A process for the preparation of (1S,2R)-1-amino-2-indanol-(R,R)-tartrate methanol solvate comprising:

reacting in a solvent a mixture of enantiomers of cis-1-amino-2-indanol at an elevated temperature with (R,R)-tartaric acid and methanol to form a reaction mixture, such that (1S,2R)-1-amino-2-indanol is present at a concentration of 0.02 g–0.1 g per ml of solvent;

crystallizing optically enriched (1S,2R)-1-amino-2-indanol-(R,R)-tartrate methanol solvate from the reaction mixture; and recovering crystals of (1S,2R)-1-amino-2-indanol-(R,R)-tartrate methanol solvate at a temperature between 10° C. and 50° C. in the presence of 0–20 wt. % water relative to the amount of methanol plus solvent, wherein the recovery takes place at a temperature between 30° C. and 50° C. if the reaction mixture is essentially free from water and wherein (1S,2R)-1-amino-2-indanol-(R,R)-tartrate is recovered in an enantiomeric excess of greater than 96% relative to (1R, 2S)-1-amino-2-indanol-(R,R)-tartrate.

2. A process according to claim 1, wherein the mixture of enantiomers of cis-1-amino-2-indanol, (R,R)-tartaric acid and methanol are at least in part contacted with each other at an elevated temperature and the reaction mixture obtained after the reaction is cooled.

3. A process according to claim 2, wherein the reaction takes place at a temperature between 55° C. and 80° C.

4. A process according to any one of claims 1–3, wherein methanol is used as solvent.

5. A process according to any one of claims 1–3, wherein additionally 2–15 wt. % of water, relative to the amount of methanol, is present in the reaction mixture.

6. A process according to claim 1, wherein the crystals are subsequently subjected to a desalting step, resulting in optically active (1S,2R)-1-amino-2-indanol.

7. (1S,2R)-1-amino-2-indanol-(R,R)-tartrate methanol solvate crystals having a particle size larger than 95 µm, measured with a Malvern 2600 apparatus and expressed as D[v, 0.9].

8. A process for the preparation of an AIDS inhibitor comprising preparing (1S,2R)-1-amino-2-indanol is prepared according to claim 7 and then converting the (1S,2R)-1-amino-2-indanol into the AIDS inhibitor.

9. A process according to claim 8, wherein said AIDS inhibitor is indinavir sulphate.

* * * * *